United States Patent
Ping et al.

(10) Patent No.: US 11,973,442 B2
(45) Date of Patent: Apr. 30, 2024

(54) PLANT PROTEIN-BASED TRIBOELECTRIC NANOGENERATOR (TENG), AND FABRICATION METHOD AND USE THEREOF

(71) Applicant: ZHEJIANG UNIVERSITY, Hangzhou (CN)

(72) Inventors: Jianfeng Ping, Hangzhou (CN); Chengmei Jiang, Hangzhou (CN); Yibin Ying, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 354 days.

(21) Appl. No.: 17/622,822

(22) PCT Filed: Nov. 25, 2019

(86) PCT No.: PCT/CN2019/112669
§ 371 (c)(1),
(2) Date: Dec. 26, 2021

(87) PCT Pub. No.: WO2020/258614
PCT Pub. Date: Dec. 30, 2020

(65) Prior Publication Data
US 2022/0352831 A1     Nov. 3, 2022

(30) Foreign Application Priority Data

Jun. 28, 2019 (CN) .......................... 201910575038.4
Jun. 28, 2019 (CN) .......................... 201910576117.7

(51) Int. Cl.
*H02N 1/04*     (2006.01)
*A61N 1/04*     (2006.01)
*C08J 5/18*     (2006.01)

(52) U.S. Cl.
CPC ................. *H02N 1/04* (2013.01); *A61N 1/04* (2013.01); *C08J 5/18* (2013.01)

(58) Field of Classification Search
CPC .. H02N 1/04; A61N 1/04; A61N 1/378; C08J 5/18
See application file for complete search history.

(56) References Cited

U.S. PATENT DOCUMENTS

2017/0359001 A1* 12/2017 Wang .................... C23C 16/045
2018/0346690 A1  12/2018 Wu et al.

FOREIGN PATENT DOCUMENTS

| CN | 104387604 A | 3/2015 |
|---|---|---|
| CN | 107800323 A | 3/2018 |

(Continued)

OTHER PUBLICATIONS

Ting-Hao Chang, et al., Protein-based contact electrification and its uses for mechanical energy harvesting and humidity detecting, Nano Energy, 2016, pp. 238-246, vol. 21.

*Primary Examiner* — Bernard Rojas
(74) *Attorney, Agent, or Firm* — Bayramoglu Law Offices LLC

(57) ABSTRACT

A plant protein-based triboelectric nanogenerator (TENG), and a fabrication method and use thereof are provided. The TENG includes a triboelectric negative layer and a protein film, where the protein film and the triboelectric negative layer are stacked surface-to-surface; and an electrode is adhered to or plated on a back surface of each of the protein film and the triboelectric negative layer, or only a back surface of either of the protein film and the triboelectric negative layer is provided with a grounded electrode. A protein powder is dissolved in water or an ethanol aqueous solution, then a plasticizing agent is added, and the protein is denatured through thermal treatment to obtain an extended structure required for film formation; and the solvent is (Continued)

Vertical contact-separation mode

Horizontal slip mode

Single electrode mode

Independent layer mode evaporated, and a resulting product is dried to obtain the protein film with uniform texture and excellent transparency and flexibility. The TENG is used in crop growth.

9 Claims, 4 Drawing Sheets

(56) References Cited

FOREIGN PATENT DOCUMENTS

| | | | |
|---|---|---|---|
| CN | 110311586 A | 10/2019 | |
| CN | 110387056 A | 10/2019 | |
| CN | 117024828 A * | 11/2023 | |
| WO | WO-2022041465 A1 * | 3/2022 | ............... C07K 1/02 |

* cited by examiner

PLANT PROTEIN-BASED TRIBOELECTRIC NANOGENERATOR (TENG), AND FABRICATION METHOD AND USE THEREOF

CROSS REFERENCE TO RELATED APPLICATIONS

This application is the national stage entry of International Application No. PCT/CN2019/112669, filed on Nov. 25, 2019, which is based upon and claims priority to Chinese Patent Application No. 201910575038.4 filed on Jun. 28, 2019, and Chinese Patent Application No. 201910576117.7 filed on Jun. 28, 2019, the entire contents of which are incorporated herein by reference.

TECHNICAL FIELD

The present disclosure relates to a triboelectric nanogenerator (TENG), and in particular to a plant protein-based TENG and a fabrication method thereof.

BACKGROUND

With the rapid development of flexible and portable electronic products, TENGs that can effectively convert mechanical energy of various forms into electrical energy will become the mainstream energy supply in the future world. So far, most of the research related to TENGs has emphasized structural design or material innovation.

Currently, materials widely used in TENGs include polyamide (nylon)-11 and polyethylene terephthalate (PET). It should be noted that these materials cannot be completely degraded and are easy to generate harmful chemicals. Since electronic products are rapidly upgraded, the old electronic products are replaced and discarded, which generates a large number of electronic waste, and undoubtedly brings a huge burden to the environment. Therefore, flexible devices made of biodegradable and non-toxic materials have received more and more attention.

In recent years, triboelectric nanogenerators (TENGs) made of a variety of biological materials such as starch, chitosan, silk nanofibers, gelatin, and bacterial nanocellulose (BNC) have been widely used in implantable devices, medical care, environmental monitoring, and other fields. However, the biological materials-based TENG is still at its early stage, and hardly feasible in practice due to the cumbersome processing steps, low-output performance, and limited choice of material. So far, there has been no use of plant proteins in TENGs, and triboelectrification properties and mechanisms still need to be explored.

SUMMARY

In order to solve the problems in the background art and fill the gaps, the present disclosure introduces a plant protein as a new triboelectric material into the field of TENGs, and innovatively uses a plant protein-based TENG as a biodegradable mulching film in a space electric field growth-promoting system. Such a TENG can be used to collect mechanical energy in the environment, and can also be used as a biodegradable mulching film in a space electric field growth-promoting system.

The present disclosure adopts the following technical solutions:

1. A plant protein-based TENG:

The TENG includes a triboelectric negative layer and a plant protein film, where the plant protein film serves as a triboelectrification electron-donating layer; the plant protein film and the triboelectric negative layer are stacked surface-to-surface; and an electrode is adhered to or plated on a back surface of each of the plant protein film and the triboelectric negative layer, or only a back surface of either of the plant protein film and the triboelectric negative layer is provided with a grounded electrode.

The present disclosure proposes for the first time that a plant protein film can be used for triboelectric material, and also proposes for the first time that the plant protein-based TENG can be used to act on the growth of biological tissues.

The plant protein film is made through the following process: dissolving an insoluble protein powder in water (when the insoluble protein powder is added in water, a pH is adjusted to be away from an isoelectric point to make the protein uniformly dispersed) or an ethanol aqueous solution, adding a plasticizing agent (which can reduce the interaction among protein molecules such that a resulting film has improved stretchability and flexibility and is not prone to drying or cracking), and denaturing the protein through thermal treatment at a temperature higher than a glass-transition temperature to obtain an extended structure required for film formation (in this process, a protein chain enhances a network structure strength of a plant protein film through the formation of hydrogen bonds, ionic bonds, covalent bonds, and hydrophobic interactions, including promoting the oxidation of mercapto into a disulfide bond to enhance the network strength of the plant protein film); and evaporating the solvent, and drying to obtain the plant protein film with uniform texture and excellent transparency and flexibility.

The triboelectric negative layer may be made of a material selected from the group consisting of polytetrafluoroethylene (PTFE, Teflon), polydimethylsiloxane (PDMS), polyvinyl chloride (PVC), polyimide (PI, Kapton), silicone rubber (Ecoflex), and polylactic acid (PLA), etc.

2. A fabrication method of the plant protein-based TENG:

The fabrication method includes the following steps: 1. preparation of a plant protein film (a triboelectrification electron-donating layer): dissolving an insoluble protein powder in water (when the insoluble protein powder is added in water, a pH is adjusted to be away from an isoelectric point to make the protein uniformly dispersed) or an ethanol aqueous solution, adding a plasticizing agent (which can reduce the interaction among protein molecules such that a resulting film has improved stretchability and flexibility and is not prone to drying or cracking), and denaturing the protein through thermal treatment at a temperature higher than a glass-transition temperature to obtain an extended structure required for film formation (in this process, a protein chain enhances a network structure strength of a plant protein film through the formation of hydrogen bonds, ionic bonds, covalent bonds, and hydrophobic interactions, including promoting the oxidation of mercapto into a disulfide bond to enhance the network strength of the plant protein film); and evaporating the solvent, and drying to obtain the plant protein film with uniform texture and excellent transparency and flexibility; stacking the plant protein film and a triboelectric negative layer surface-to-surface; and adhering or plating an electrode to or on a back surface of each of the plant protein film and the triboelectric negative layer, or only arranging a grounded electrode on a back surface of either of the plant protein film and the triboelectric negative layer.

The protein powder may be a powder of rice protein, peanut protein isolate (PPI), soy protein isolate (SPI), glutenin, or zein.

The plasticizing agent may be a polyol (glycerin, propylene glycol (PG), ethylene glycol (EG), sorbitol, and polyethylene glycol (PEG)).

The triboelectric negative layer may be made of a material selected from the group consisting of PTFE (Teflon), PDMS, PVC, PI (Kapton), silicone rubber (Ecoflex), and PLA, etc.

The step 1) may specifically include: dispersing the protein in an aqueous solution or an ethanol aqueous solution with a concentration of 70% to 90% to prepare a protein solution (a mass fraction of the protein is 1% to 10%, w/w), and adding the plasticizing agent (such as glycerin) at a mass 10% to 60% of a mass of the protein (w/w) to the protein solution; stirring a resulting mixture in a 60° C. to 95° C. water bath for 30 min to 60 min to conduct protein denaturation, and degassing under vacuum for 10 min; and pouring a resulting solution into a mold, and placing the mold in an oven to conduct evaporation drying at 30° C. to 70° C.

The protein may be rice protein, PPI, SPI, or glutenin; and specifically: mixing a protein with glycerin in a deionized water solution, magnetically stirring a resulting mixture, and adjusting a pH of a resulting protein solution to 12 with a 1 M sodium hydroxide solution; and heating and stirring the protein solution at 65° C. for 30 min, and degassing under vacuum for 10 min to remove bubbles.

The protein may be zein; and specifically: dissolving zein and glycerin in an ethanol aqueous solution with a mass concentration of 70%, directly heating and stirring a resulting protein solution at 65° C. for 30 min, and degassing under vacuum for 10 min.

The present disclosure also provides use of the TENG in crop growth, which plays a role in promoting the growth of crops. The TENG may be placed on soil, with the plant protein film contacting the soil; and then a force may be applied to the TENG to make the triboelectric negative layer approach, leave, or slip relative to the plant protein film, thereby generating an electric field to promote crop growth.

As shown in FIG. 4, the TENG of the present disclosure can have four working modes: vertical contact-separation mode, lateral-sliding mode, single-electrode mode, and freestanding triboelectric-layer mode.

Vertical contact-separation mode: In this structure, the plant protein film and the triboelectric negative layer are stacked surface-to-surface, and an electrode is adhered to or plated on a back surface of each of the plant protein film and the triboelectric negative layer. When the triboelectric negative layer and the plant protein film are in contact with each other, surface charges with opposite signs are formed on the two contact surfaces. When the two surfaces are separated, a small air gap is formed therebetween, and an induced potential difference is formed between the two electrodes. When the two electrodes are connected through a load, electrons will flow from one electrode to the other through the load, thereby forming a reverse potential difference to balance the electrostatic field. When the air gap between the triboelectric negative layer and the plant protein film is eliminated due to an external force, the potential difference formed by triboelectric charges disappears, and electrons will flow back. In this way, the electric field that changes over time will drive electrons to flow back and forth between the electrode on the back surface of the plant protein film and the electrode on the back surface of the triboelectric negative layer, thereby generating alternating current (AC).

Lateral-sliding mode: The initial structure of this mode is the same as the vertical contact-separation mode, that is, the plant protein film and the triboelectric negative layer are stacked surface-to-surface, an electrode is adhered to or plated on a back surface of each of the plant protein film and the triboelectric negative layer, and the two electrodes are connected to each other through an external circuit. When the plant protein film is in contact with the triboelectric negative layer, a relative slip occurs between the two materials in a horizontal direction parallel to the surface, which can also lead to the generation of triboelectric charges on the two surfaces. In this way, polarization will be formed in the horizontal direction, which can drive electrons to flow between the electrode on the back surface of the plant protein film and the electrode on the back surface of the triboelectric negative layer to balance the electrostatic field resulting from the triboelectric charges. Through periodic slip separation and closing, an AC output can be produced. This is the basic principle of the slip TENG, and the slip can exist in many forms, including plane slip, cylindrical slip, and disc slip.

Single electrode mode: The plant protein film and the triboelectric negative layer are combined together, and then a grounded electrode layer is arranged on a back surface of either of the plant protein film and the triboelectric negative layer to form the TENG. When the upper triboelectric negative layer approaches or leaves the lower plant protein film, or when the upper triboelectric negative layer frictionally moves relative to the lower plant protein film, the local electric field distribution will change, and thus there will be an electron exchange between the electrode and the ground to balance the potential change on the electrode.

Freestanding triboelectric-layer mode: Two unconnected symmetrical electrodes are adhered to or plated on the back surface of the plant protein film, and then the two electrodes are connected through an external circuit. The sizes of and the spacing between the electrodes can be appropriately controlled. When the triboelectric negative layer reciprocates between the two electrodes on the surface of the plant protein film, a potential difference between the two electrodes will change, which in turn drives electrons to flow back and forth between the two electrodes through the external circuit load to balance the change of the potential difference.

3. Use of the TENG of the present disclosure in crop growth, which plays a role in promoting the growth of crops. The TENG may be placed on soil, with the plant protein film contacting the soil; and then a force may be applied to the TENG to make the triboelectric negative layer approach, leave, or slip relative to the plant protein film, thereby generating an electric field to promote crop growth.

Compared with the prior art, the present disclosure has the following beneficial effects:

1. The biological material of plant protein has never been introduced into the field of TENGs before. Because there are many amino and hydroxyl groups on the surface of plant protein, plant protein has strong electron-donating ability and is a natural candidate material for TENG.
2. Compared with other biological materials, plant protein is widely present, cheap, and often discarded as waste, and can be easily made into a plant protein film.
3. The fabricated plant protein-based TENG is used for the first time as a mulching film in the agricultural space electric field growth-promoting system. The plant protein-based TENG shows prominent technical effects on tested bean sprouts, and thus has promising application prospects.

The present disclosure innovatively uses a plant protein as a triboelectric material (using various plant proteins for triboelectric behaviors, including rice protein, PPI, SPI, glutenin, and zein), and innovatively uses a TENG as a biodegradable mulching film to create a space electric field growth-promoting system for agriculture, and considerable technical achievements have been made.

Figure 1A:
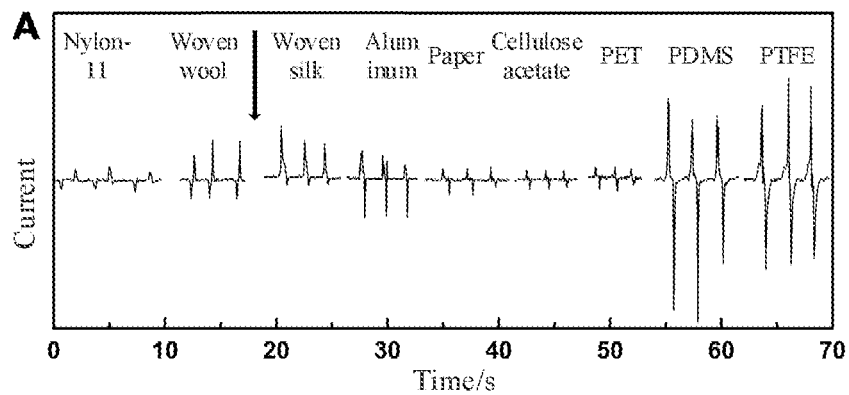
FIG. 1A shows the arrangement positions of rice protein in a triboelectric sequence of common materials determined according to a direction of an output current signal in an example of the present disclosure.
Figure 1B:
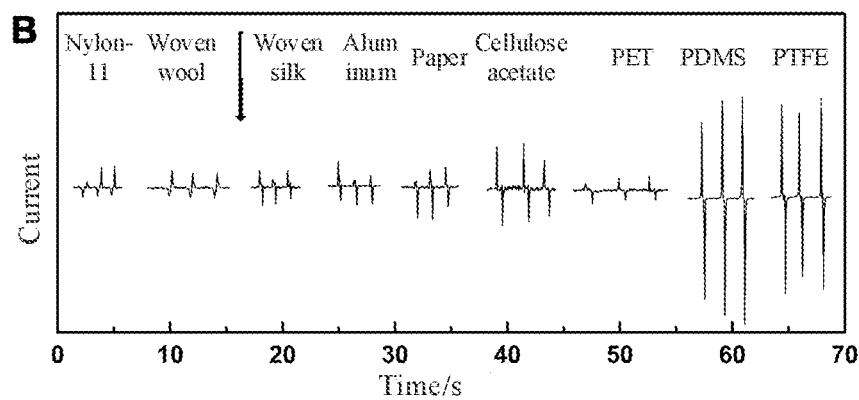
FIG. 1B shows the arrangement positions of PPI in a triboelectric sequence of common materials determined according to a direction of an output current signal in an example of the present disclosure.
Figure 1C:
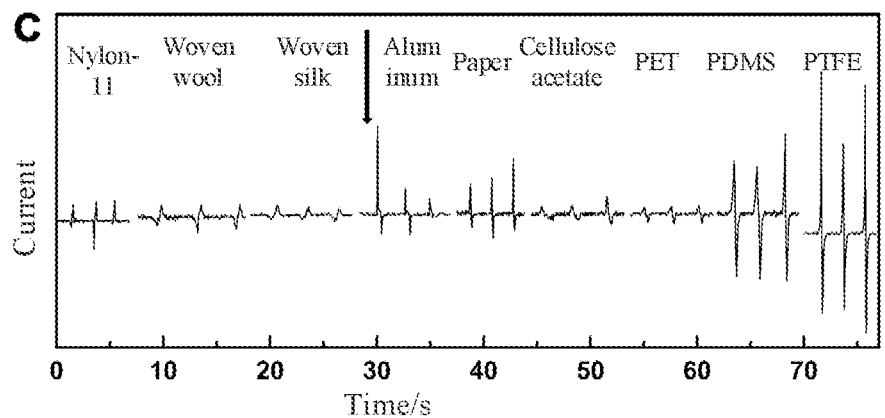
FIG. 1C shows the arrangement positions of SPI in a triboelectric sequence of common materials determined according to a direction of an output current signal in an example of the present disclosure.
Figure 1D:
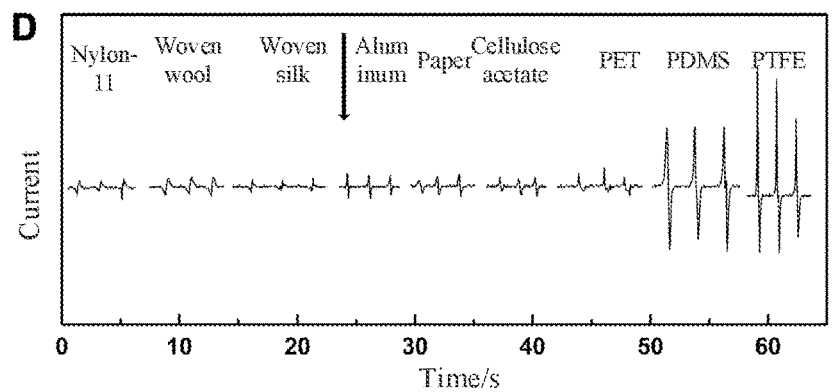
FIG. 1D shows the arrangement positions of glutenin in a triboelectric sequence of common materials determined according to a direction of an output current signal in an example of the present disclosure.
Figure 1E:
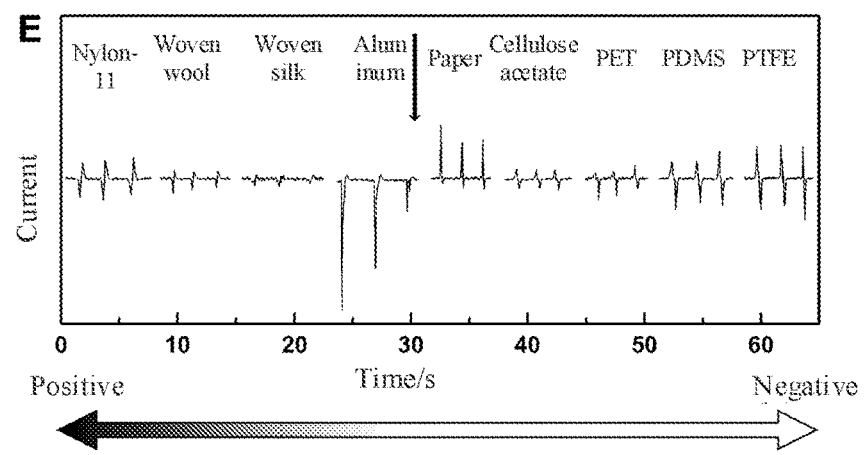
FIG. 1E shows the arrangement positions of zein in a triboelectric sequence of common materials determined according to a direction of an output current signal in an example of the present disclosure.

Table 1 shows the technical effect of the present disclosure on bean sprouts (research object), where the plant protein-based TENG is used as a mulching film to harvest mechanical energy in the environment and generate an electric field from the mechanical energy for a growth-promoting system.

DETAILED DESCRIPTION OF THE EMBODIMENTS

The present disclosure is described in further detail below with reference to the accompanying drawings and examples.

Specific implementations of the present disclosure:

1) Preparation of a plant protein film: A protein is dispersed in an aqueous solution or an ethanol aqueous solution with a concentration of 70% to 90% to prepare a protein solution (1% to 10%, w/w), and a plasticizing agent (such as glycerin) is added at a mass 10% to 60% of a mass of the protein (w/w) to the protein solution; a resulting mixture is stirred in a 60° C. to 95° C. water bath for 30 min to 60 min to conduct protein denaturation, and then subjected to degassing under vacuum for 10 min; and a resulting solution is poured into a mold, and then subjected to evaporation drying at 30° C. to 70° C. in an oven.

In a specific implementation, a dried plant protein film is finally peeled off and placed under constant temperature and humidity conditions, such that the plant protein film has an equilibrium moisture content and is ready for subsequent electrical tests.

2) Triboelectric negative layer: The triboelectric negative layer is specifically made of a material selected from the group consisting of PTFE (Teflon), PDMS, PVC, PI (Kapton), silicone rubber (Ecoflex), and PLA.

In an implementation of the present disclosure, the plant protein film and a common test material from triboelectric series (nylon-11, woven wool, woven silk, aluminum, paper, cellulose acetate, PET, PDMS, and PTFE) are combined to form a triboelectric pair to test the electron-donating ability. A specific operation method is as follows: a test material is arranged above the plant protein film, an electrode is arranged at a bottom of the plant protein film, and the electrode is grounded; when the test material is in contact with or separated from the plant protein film, a multimeter is used to test the generated current signal; and a current direction is determined according to whether the current signal is positive or negative, thus to determine a flow direction of electrons and determine the polarity of charges on surfaces of the test material and the plant protein film, thereby inferring the electron-donating ability of the test material and the plant protein film.

As shown in FIGS. 1A-1E, the five plant protein films (rice protein, PPI, SPI, glutenin, and zein) are each subjected to a comparison test with triboelectric series of the common test materials to determine positions of the five plant proteins in the triboelectric series. It can be seen from the figure that the plant protein films have relatively strong electron-donating ability, which ranks in the top positions in the triboelectric series of the common materials.

EXAMPLES

Example 1

1) Preparation of a plant protein film: Rice protein, PPI, SPI, or glutenin was dispersed in distilled water to prepare a film-forming solution (5%, w/w), and zein was dispersed in an ethanol aqueous solution with a concentration of 70% to prepare a film-forming solution (5%, w/w). Then glycerin was added at a mass 30% of a mass of the protein (w/w) to each of the five protein solutions.

2) In this example, for rice protein, PPI, SPI, and glutenin, a specific process was as follows: 5 g of a plant protein was mixed with 1.5 g of glycerin in 100 mL of a deionized water solution, a resulting mixture was magnetically stirred for 10 min, and then the pH of protein solution was adjusted to 12 with a 1 M sodium hydroxide solution. The protein solution was heated and stirred at 65° C. for 30 min, and then subjected to degassing under vacuum for 10 min to remove bubbles.

In this example, for zein, a specific process was as follows: 5 g of zein and 1.5 g of glycerin were dissolved in 100 mL of an ethanol aqueous solution with a concentration of 70%, and a resulting protein solution was directly heated and stirred at 65° C. for 30 min, and then subjected to degassing under vacuum for 10 min.

3) A final film-forming solution was poured into a round Teflon mold (with a diameter of 3 cm) and dried in an oven at 60° C. Then the dried film was peeled off and placed for 24 h in a constant-temperature and constant-humidity incubator at 25° C. and 40% relative humidity (RH), and then tested as a triboelectrification electron-donating layer.

In the test, a triboelectric negative layer was a PDMS film. The PDMS film was prepared by thoroughly mixing an elastic agent with a curing agent in a mass ratio of 10:1 and subjecting a resulting mixture to vacuum degassing and then to curing for 20 min to 60 min in an oven at 65° C. to 95° C.

Figure 2A:
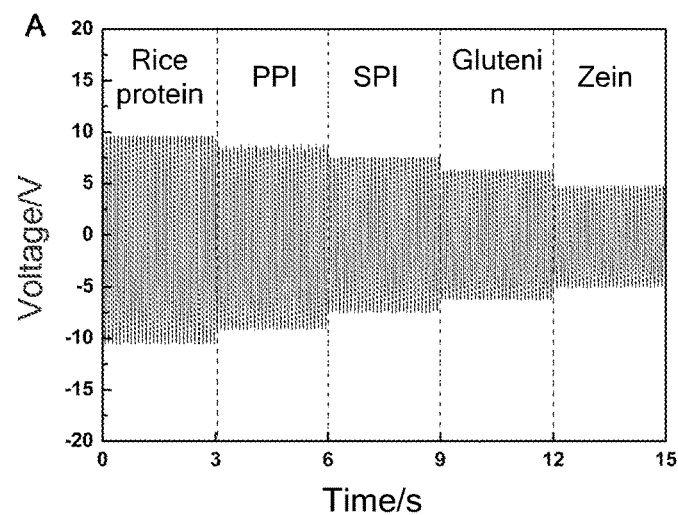
FIG. 2A shows the output performance of TENGs based on the five proteins in an example of the present disclosure, which is for the output current.
Figure 2B:
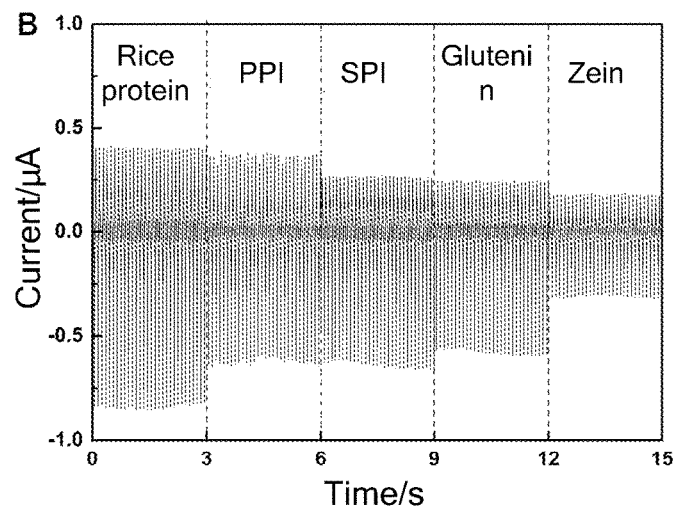
FIG. 2B shows the output performance of TENGs based on the five proteins in an example of the present disclosure, which is for the output current.

The plant protein film and the PDMS film were combined to form a triboelectric pair, and an aluminum foil was arranged as an electrode at a bottom of the PDMS film. Through the contact and separation between the plant protein film and the PDMS film, an electron flow was generated in an external circuit, and electrical tests were conducted with an electrometer and an oscillometer. As shown in FIGS. 2A-2B, the five plant protein films have different output voltages and currents, and the output signal sizes are in the same order as the electron-donating abilities, which further verifies the previous conclusion: in terms of the electron-donating ability, the four plant proteins rank from large to small as follows: rice protein, PPI, SPI, glutenin, and zein.

Example 2

Rice protein was taken as an example. 5 g of rice protein was mixed with 1.5 g of glycerin in 100 mL of a deionized water solution, a resulting mixture was magnetically stirred for 10 min, and then the pH of protein solution was adjusted to 12 with a 1 M sodium hydroxide solution. The protein solution was heated and stirred at 65° C. for 30 min, and then subjected to degassing under vacuum for 10 min to remove bubbles. A final film-forming solution was poured into a round Teflon mold (with a diameter of 3 cm) and dried in an oven at 60° C. The dried film was peeled off and placed for 24 h in a constant-temperature and constant-humidity incubator at 25° C. and 40% RH, and then tested as a triboelectrification electron-donating layer.

Fabrication of a triboelectric negative layer: A PLA film was cut into a round shape with a diameter of 3 cm.

Figure 3:
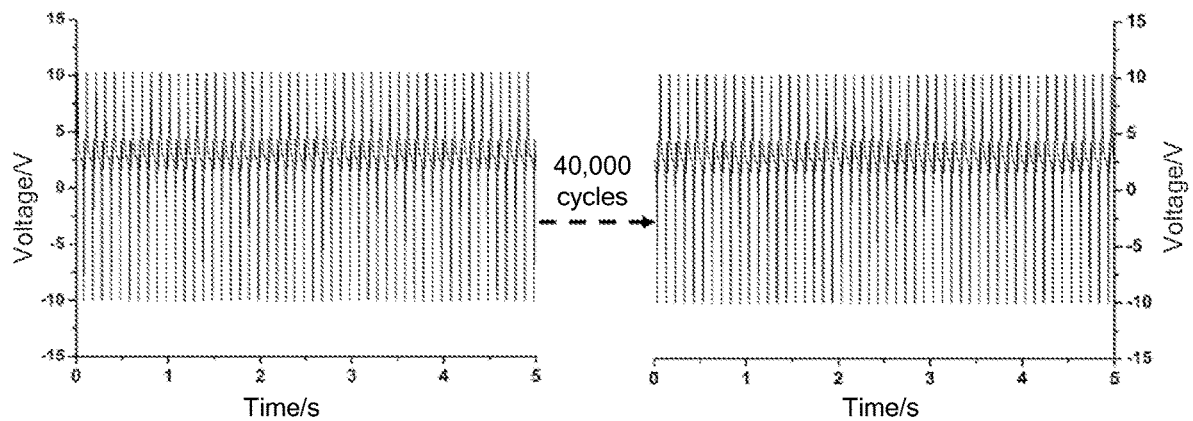
FIG. 3 shows the fatigue test results of the rice protein-based TENG in an example of the present disclosure, and it can be seen that the rice protein-based TENG still has high reliability after 40,000 continuous working cycles.
Figure 4:
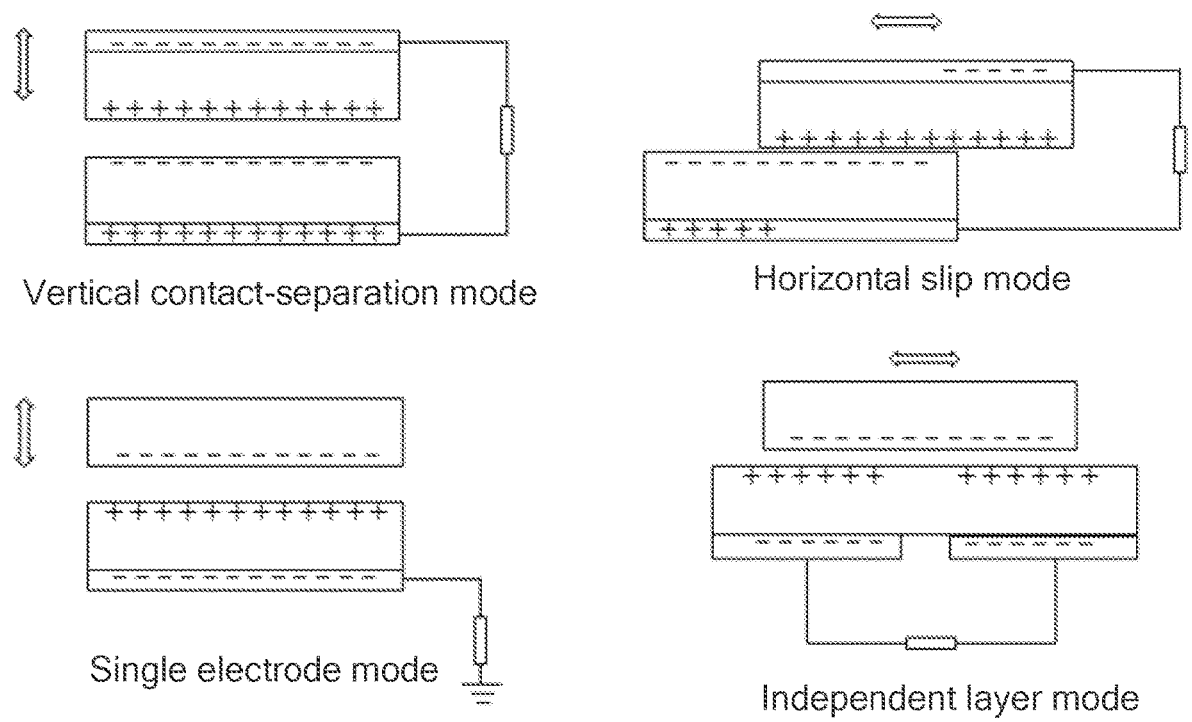
FIG. 4 is a schematic diagram of the four working modes of the present disclosure.

Fabrication of a TENG: The above rice protein film and the PLA film were combined to form a triboelectric pair, and an aluminum foil was arranged as an electrode at a side of the PLA film to form the TENG. A voltage signal of the TENG was determined with an oscillometer. As shown in FIG. 3, after 40,000 cycles, the signal was still very stable.

Example 3

5 g of zein and 1.5 g of glycerin were dissolved in 100 mL of an ethanol aqueous solution with a concentration of 70%, and a resulting protein solution was directly heated and stirred at 65° C. for 30 min, and then subjected to degassing under vacuum for 10 min. A final film-forming solution was poured into a round Teflon mold (with a diameter of 3 cm) and dried in an oven at 60° C. The dried film was peeled off and placed for 24 h in a constant-temperature and constant-humidity incubator at 25° C. and 40% RH, and then tested as a triboelectrification electron-donating layer.

Fabrication of a triboelectric negative layer: A PLA film was cut into a round shape with a diameter of 3 cm, and then poly(3,4-ethylenedioxythiophene):poly(styrene sulfonate) (PEDOT:PSS) was spin-coated on one side of the PLA film at 1,000 rpm to serve as an electrode.

The plant protein film and the PLA film were combined into a mulching film, where the PLA film spin-coated with conductive PEDOT:PSS was on the top, and the plant protein film was in contact with the soil. A specified amount of force was applied to the TENG to simulate mechanical energy in the environment. Bean sprouts were adopted as test objects. Beans were soaked for 4 h and then incubated for 3 d in a constant-temperature and constant-humidity incubator at 25° C. and 40% RH; and after the beans sprouted, bean sprouts with similar growth were selected and divided into two groups: test group and control group. The test group was placed in an electric field generated by the TENG (4 h/d); and 48 h later, an elongation and a weight gain rate (WGR) were determined for the bean sprouts to characterize the growth of the bean sprouts.

TABLE 1

| Sample No. | Test group | | Control group | |
| --- | --- | --- | --- | --- |
| | Elongation | WGR | Elongation | WGR |
| 1 | 265.0% | 16.4% | 123.1% | 10.9% |
| 2 | 161.9% | 27.5% | 98.0% | 12.5% |
| 3 | 201.7% | 28.1% | 158.1% | 17.2% |
| 4 | 272.6% | 41.2% | 167.5% | 24.4% |
| 5 | 214.8% | 27.4% | 68.4% | 25.8% |
| 6 | 162.5% | 21.2% | 192.3% | 23.8% |
| 7 | 124.0% | 18.1% | 215.2% | 12.4% |
| 8 | 152.8% | 18.9% | 169.1% | 19.9% |
| 9 | 288.9% | 21.5% | 76.8% | 17.4% |
| 10 | 224.0% | 28.6% | 176.4% | 22.4% |
| 11 | 103.7% | 16.0% | 138.4% | 16.6% |
| 12 | 192.5% | 27.2% | 0.6% | 23.9% |
| 13 | 240.0% | 22.8% | 196.1% | 14.4% |
| 14 | 148.4% | 18.0% | 139.5% | 13.9% |
| 15 | 334.3% | 25.3% | 100.1% | 19.4% |
| 16 | 197.2% | 16.6% | 232.7% | 19.9% |
| 17 | 324.1% | 35.0% | 117.3% | 24.8% |
| 18 | 405.2% | 30.9% | 118.1% | 15.4% |
| 19 | 181.2% | 19.9% | 88.6% | 15.4% |
| 20 | 318.1% | 28.5% | 144.8% | 17.6% |
| 21 | 352.4% | 27.1% | 105.3% | 28.6% |
| 22 | 172.9% | 18.2% | 122.3% | 21.4% |
| 23 | 93.9% | 20.1% | 69.6% | 17.9% |
| 24 | 239.9% | 27.6% | 160.3% | 23.1% |
| Average value | 223.8% | 24.3% | 132.4% | 19.1% |
| Standard deviation (SD) | 82.3% | 6.4% | 53.1% | 4.8% |

It can be seen from Table 1 above that the electric field generated by the TENG has a significant promotion effect on the growth of bean sprouts, indicating that the plant protein-based TENG can be used as a mulching film in the agricultural space electric field growth-promoting system.

What is claimed is:

1. A plant protein-based triboelectric nanogenerator (TENG), comprising a triboelectric negative layer and a plant protein film, wherein the plant protein film and the triboelectric negative layer are stacked in a surface-to-surface manner; and an electrode is adhered to or plated on a back surface of each of the plant protein film and the triboelectric negative layer, or the back surface of either of the plant protein film and the triboelectric negative layer is provided with a grounded electrode, wherein the triboelectric negative layer is made of a material selected from the group consisting of polytetrafluoroethylene (PTFE), polydimethylsiloxane (PDMS), polyvinyl chloride (PVC), polyimide (PI), silicone rubber, and polylactic acid (PLA).

2. The plant protein-based TENG according to claim 1, wherein the plant protein film is made by the following method: dissolving a protein powder in water or an ethanol aqueous solution, adding a plasticizing agent, and denaturing the protein through thermal treatment to obtain an extended structure required for film formation; and evaporating a solvent, and drying to obtain the plant protein film with uniform texture and excellent transparency and flexibility.

3. A method of using a plant protein-based triboelectric nanogenerator (TENG) in crop growth, the plant protein-based TENG comprising a triboelectric negative layer and a plant protein film, wherein the plant protein film and the triboelectric negative layer are stacked in a surface-to-surface manner; and an electrode is adhered to or plated on a back surface of each of the plant protein film and the triboelectric negative layer, or the back surface of either of the plant protein film and the triboelectric negative layer is provided with a grounded electrode, the method comprising:
  placing the plant protein-based TENG on a soil, with the plant protein film contacting the soil; and
  applying a force to the plant protein-based TENG to make the triboelectric negative layer approach, leave, or slip relative to the plant protein film, to generate an electric field to promote crop growth.

4. A fabrication method of a plant protein-based triboelectric nanogenerator (TENG), comprising:
  step 1) preparation of a plant protein film: dissolving a protein powder in water or an ethanol aqueous solution, adding a plasticizing agent, and denaturing the protein through thermal treatment to obtain an extended structure required for film formation; evaporating the solvent, and drying to obtain the plant protein film with uniform texture and excellent transparency and flexibility;
  step 2) stacking the plant protein film and a triboelectric negative layer in a surface-to-surface manner; and
  step 3) adhering or plating an electrode on a back surface of each of the plant protein film and the triboelectric negative layer, or arranging a grounded electrode on the back surface of either of the plant protein film and the triboelectric negative layer, wherein the protein powder is a powder of rice protein, peanut protein isolate (PPI), soy protein isolate (SPI), glutenin, or zein.

5. The fabrication method of a plant protein-based TENG according to claim 4, wherein the plasticizing agent is a polyol, comprising glycerin, propylene glycol (PG), ethylene glycol, sorbitol, and polyethylene glycol (PEG).

6. The fabrication method of a plant protein-based TENG according to claim 4, wherein the triboelectric negative layer is made of a material selected from the group consisting of PTFE, PDMS, PVC, PI, silicone rubber, and PLA.

7. The fabrication method of a plant protein-based TENG according to claim 4, wherein step 1) specifically comprises:
  dispersing the protein powder in the water or the ethanol aqueous solution with a concentration of 70% to 90% to prepare a protein solution, wherein a mass fraction of the protein is 1% to 10% w/w;
  adding the plasticizing agent at a mass 10% to 60% of a mass of the protein to the protein solution;
  stirring a resulting mixture in a 60° C. to 95° C. water bath for 30 min to 60 min to conduct protein denaturation, and degassing under vacuum for 10 min; and
  pouring a resulting solution into a mold, and placing the mold in an oven to conduct evaporation drying at 30° C. to 70° C.

8. The fabrication method of a plant protein-based TENG according to claim 4, wherein the protein is rice protein, PPI, SPI, or glutenin; and step 1) specifically comprises:
  mixing a protein with glycerin in a deionized water solution, magnetically stirring a resulting mixture, and adjusting a pH of a resulting protein solution to 12 with a 1 M sodium hydroxide solution; and
  heating and stirring the resulting protein solution at 65° C. for 30 min, and degassing under vacuum for 10 min to remove bubbles.

9. The fabrication method of a plant protein-based TENG according to claim 4, wherein the protein is zein; and step 1) specifically comprises:
  dissolving zein and glycerin in the ethanol aqueous solution with a mass concentration of 70%,
  directly heating and stirring a resulting protein solution at 65° C. for 30 min, and
  degassing under vacuum for 10 min.

* * * * *